(12) United States Patent
Simopoulos (10) Patent No.: US 8,435,180 B2
(45) Date of Patent: May 7, 2013

(54) GAIN OPTIMIZATION OF VOLUME IMAGES FOR MEDICAL DIAGNOSTIC ULTRASONIC IMAGING

(75) Inventor: Constantine Simopoulos, San Francisco, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1221 days.

(21) Appl. No.: 11/901,675

(22) Filed: Sep. 17, 2007

(65) Prior Publication Data

US 2009/0076387 A1 Mar. 19, 2009

(51) Int. Cl.
*A61B 8/00* (2006.01)

(52) U.S. Cl.
USPC ............... 600/437; 600/407; 382/128

(58) Field of Classification Search .......... 600/407, 600/437; 382/170–171, 128, 165, 168
See application file for complete search history.

(56) References Cited

U.S. PATENT DOCUMENTS

| | | | |
|---|---|---|---|
| 4,852,576 A | 8/1989 | Inbar et al. | |
| 5,579,768 A * | 12/1996 | Klesenski | 600/442 |
| 5,899,863 A * | 5/1999 | Hatfield et al. | 600/443 |
| 5,910,115 A | 6/1999 | Rigby | |
| 6,021,213 A * | 2/2000 | Helterbrand et al. | 382/128 |
| 6,246,784 B1 * | 6/2001 | Summers et al. | 382/128 |
| 6,579,238 B1 | 6/2003 | Simopoulos et al. | |

* cited by examiner

*Primary Examiner* — Tse Chen
*Assistant Examiner* — Joel F Brutus (57) ABSTRACT

Tissue information is equalized by adaptively controlling gain and mapping input data to output data based on the gain in three-dimensional medical diagnostic imaging. A hypersurface is fit in three spatial dimensions to tissue information in input data. The hypersurface is used to adjust the gain so that input values are mapped to output values with more uniform soft tissue levels.

16 Claims, 4 Drawing Sheets

GAIN OPTIMIZATION OF VOLUME IMAGES FOR MEDICAL DIAGNOSTIC ULTRASONIC IMAGING

BACKGROUND

The present embodiments relate to medical diagnostic ultrasonic imaging, and in particular, to systems that adaptively set one or more stages of back-end mapping that may include gain, dynamic range and post-processing map stages to improve such imaging.

In conventional ultrasonic imaging, a B-mode signal is adjusted for gain and dynamic range before the B-mode signal is mapped to a range of gray levels or colors for display. The dynamic range of the signal to be displayed can conventionally be set by the user by a display dynamic range control. This control is conventionally independent of range and azimuthal position in the image. The gain can conventionally be varied by the user using depth gain compensation (DGC) or time gain compensation (TGC) control along with the master gain or B gain control. The DGC and TGC controls are conventionally variable in range (axial dimension) only, and the master gain is independent of both range and lateral (azimuthal) position. A few systems also offer lateral gain compensation in addition to depth gain compensation, but the two one-dimensional gain controls comprise only an approximation to a true two-dimensional gain control.

After gain and display dynamic range have been applied, log-compressed B-mode signals are re-quantized, typically to 8-bit or 256 quantization levels. The quantization step (in dB) is given by the ratio of the dynamic range selected by the user to the number of quantization levels.

After quantization, a post-processing map is used to map the quantization levels to a range of gray levels or colors. This map can be a selected one of a predesigned set of maps or alternately a user-designed map. These maps are also conventionally range and azimuth independent.

On commercially available ultrasound imaging systems, gain controls are often used by the users to adjust the brightness level. In many cases, users adjust the gain mainly to keep the regional mean of the soft tissue gray level within a narrow range of gray values across the image. This preferred range is consistent from user to user, and in many cases users tend to adjust the gain to set the gray level for soft tissue roughly to the 64th gray level on a linear map that maps 0 to black and 255 to white.

The gain adjustments may work well for two-dimensional imaging given the user interface. Overall gain is controlled by a knob or single setting applied to all data. TGC or DGC are controlled by sliders representative of different depths. However, spatial variation in three-dimensions is difficult to implement on a user interface.

U.S. Pat. No. 6,579,238 discloses various embodiments for automatically setting the gain, dynamic range, and mapping. These parameters may be optimized by fitting a surface for imaging.

SUMMARY

By way of introduction, the preferred embodiments described below include methods, systems, instructions, and computer readable media for equalizing tissue information, adaptively controlling gain, and/or mapping input data to output data in three-dimensional medical diagnostic imaging. A hypersurface is fit in three spatial dimensions to input data. The hypersurface is used to adjust gain so that input values are mapped to output values with more uniform soft tissue levels.

In a first aspect, a medical ultrasonic imaging system implements a method for adaptively controlling gain. Voxels of input volume data corresponding to soft tissue are identified. A three-dimensional hypersurface is fit to the voxels corresponding to soft tissue. A gain of the system is adaptively varied as a function, at least in part, on the fitted hypersurface.

In a second aspect, a system is provided for equalizing tissue information in medical diagnostic ultrasound imaging. A processor is operable to determine a hypersurface as a function of data representing a volume and operable to map the data to output values as a function of the hypersurface. A display is operable to display an image responsive to the output values.

In a third aspect, a computer readable storage medium has stored therein data representing instructions executable by a programmed processor for mapping input data to output data in medical diagnostic imaging. The storage medium includes instructions for extracting spatial variations in intensity with a three-dimensional hypersurface embedded in four dimensional space, the four dimensional space comprising three spatial dimensions and a fourth intensity dimension, mapping the input data to the output data as a function of the hypersurface, and displaying an image as a function of the output data.

The present invention is defined by the following claims, and nothing in this section should be taken as a limitation on those claims. Further aspects and advantages of the invention are discussed below in conjunction with the preferred embodiments and may be later claimed independently or in combination.

DETAILED DESCRIPTION OF THE PRESENTLY PREFERRED EMBODIMENTS

The intensities associated with voxels representing a volume are adaptively adjusted so that tissue with similar echogenicity has more uniform intensity level throughout the volume. Variations of the intensity due to differences of the absorption properties of intervening tissue are compensated. Rather than requiring manual adjustment of component two-dimensional frames of data forming the volume, the adaptive adjustment is automatic. Rather than requiring automatic adjustment on the component two-dimensional frames of data without regard to the overall volume, the adaptive adjustment is a function of the volume data.

Data of the volume associated with soft tissue is identified. For example, the first, second, or higher moments of the probability distribution of the signal is estimated using a volume kernel (e.g., 3×3×3) around each voxel or datum. A hypersurface is fit to the intensities or data for the soft tissue. The hypersurface is embedded in a four dimensional space with three spatial dimensions and a fourth dimension for intensity. The hypersurface is described by a polynomial or other function to provide a slowly varying intensity adjustment throughout the volume. A difference of the hypersurface from a target intensity for each location in the volume is calculated as a gain for each voxel of the volume. The data of the volume or other volumes is mapped to output data using the gains.

In one embodiment, the systems or methods of U.S. Pat. No. 6,579,238, the disclosure of which is incorporated herein by reference, implement the hypersurface gain adjustment and/or mapping. Other features of the systems and methods, such as dynamic range adjustment and/or noise compensation, may or may not be used. In other embodiments, the hypersurface gain adjustment and/or mapping is used in systems and methods different than described in U.S. Pat. No. 6,579,238.

Note that the terms "input data," or "volume data" is used broadly to refer to amplitude, intensity or log-compressed amplitude of the beamformer output (i.e. B-mode signal) as well as to any parameter of interest derived or extracted from the beamformer output, including the average velocity and power estimates of the Doppler frequency shift (i.e. Color Doppler Mode signals) and the power spectrum estimate of the Doppler frequency shift (i.e., Spectral Doppler Mode signals).

Figure 1:
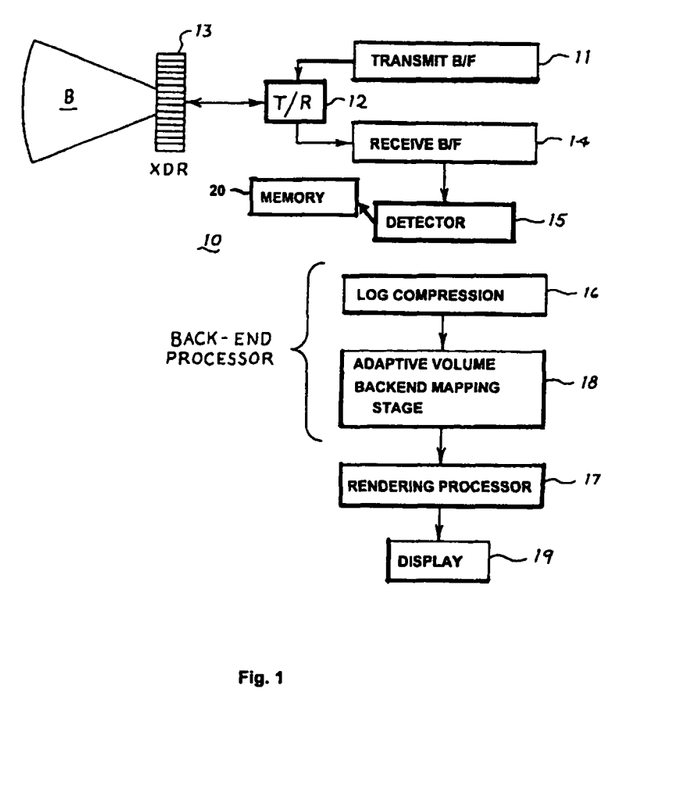
FIG. 1 is a block diagram of a medical diagnostic ultrasonic imaging system that incorporates one embodiment.

Turning now to the drawings, FIG. 1 is a block diagram of a medical diagnostic ultrasonic imaging system 10 for equalizing tissue information. As shown in FIG. 1, a transmit beamformer 11 applies transmit waveforms via a transmit/receive switch 12 to a transducer array 13. The transducer array 13 produces ultrasonic pulses in response to the transmit waveforms, which pulses are directed into a body B to be imaged. Returning echoes from the body B impinge upon the transducer array 13, which converts these echoes into receive signals that are transmitted via the transmit/switch 12 to a receive beamformer 14. The receive beamformer 14 applies appropriate delays and/or phase shifts to cause the receive signals from selected locations within the body B to add coherently. These beamformed signals are applied to an amplitude detector 15 and a back-end processor that includes a log compression device 16 before being applied to a rendering processor 17.

The rendering processor 17 is a graphic processing unit, graphics board, graphics chip, general processor, application specific integrated circuit, digital signal processor, field programmable gate array, analog circuit, digital circuit, or other now known or later processor for rendering. The rendering processor 17 receives the volume data after mapping. The received data is a complete volume data set. Alternatively, the data is received as the data is mapped, such as mapping the data as needed during the rendering. The rendering processor 17 generates display values upon a grid appropriate for a display 19. The display values are responsive to output values from the back-end processor. The rendering processor 17 implements ray casting, surface rendering, or other now known or later developed volume rendering.

A memory 20 receives data from the detector 15 and outputs data to the back-end processor. The memory 20 may be positioned at other locations, such as between the log compression 16 and the mapping stage 18. The memory 20 is a single device, but may be a collection of two or more devices each used for a same or different purpose.

Data representing a volume is stored in the memory 20. Each input datum (e.g., intensity) is a voxel. The data is interpolated or formed on an evenly spaced three-dimensional grid. Alternatively, the data of the volume is anisotropic, such as each voxel having a larger size along at least one dimension. In other embodiments, the voxels are along a polar coordinate grid, such as associated with receiving parallel or non-parallel two-dimensional frames of data within the volume.

The memory 20 may also be a computer readable storage medium having stored therein data representing instructions executable by a programmed processor. The memory 14 and/or another memory store instructions for operating the back-end processor, such as the mapping stage 18. The instructions are for mapping input data to output data in medical diagnostic imaging. The instructions for implementing the processes, methods, and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

All of the elements 11-17 and 19-20 can take any suitable form, and are not limited to any particular implementation. For example, the transmit and receive beamformers can be constructed as analog or digital devices, and any suitable transducer array can be used, including a single-element transducer array and phased arrays of various dimensions. In addition, the system 10 may include additional elements in the signal path between the transducer array 13 and the display 19, and selected ones of the illustrated elements may be deleted or the order of some of the elements may be switched. For example the order of the back-end processor and rendering processor 17 can be altered, such as providing scan conversion before the memory 20 so that scan converted frames of data are used to represent the volume. As another example, the rendering processor 17 is in a separate computer.

The back-end processor also includes the adaptive multi-dimensional back-end mapping stage 18. This mapping stage 18 can take many forms, such as any of the embodiments disclosed in U.S. Pat. No. 6,579,238. Any combination of functions and corresponding embodiments of U.S. Pat. No. 6,579,238 may be used. Noise, signal-to-noise ratio, dynamic range processing, tissue identification, gain, mapping, fitting, or other aspects may be used as disclosed in U.S. Pat. No. 6,579,238, but based on volume data. Other embodiments are provided below.

The mapping stage 18 is a processor for mapping input volume data to output volume data. The processor is a general processor, digital signal processor, application specific integrated circuit, field programmable gate array, memory, digital circuit, analog circuit, combinations thereof, or other now known or latter developed component or components for mapping input data to output data.

Figure 2:
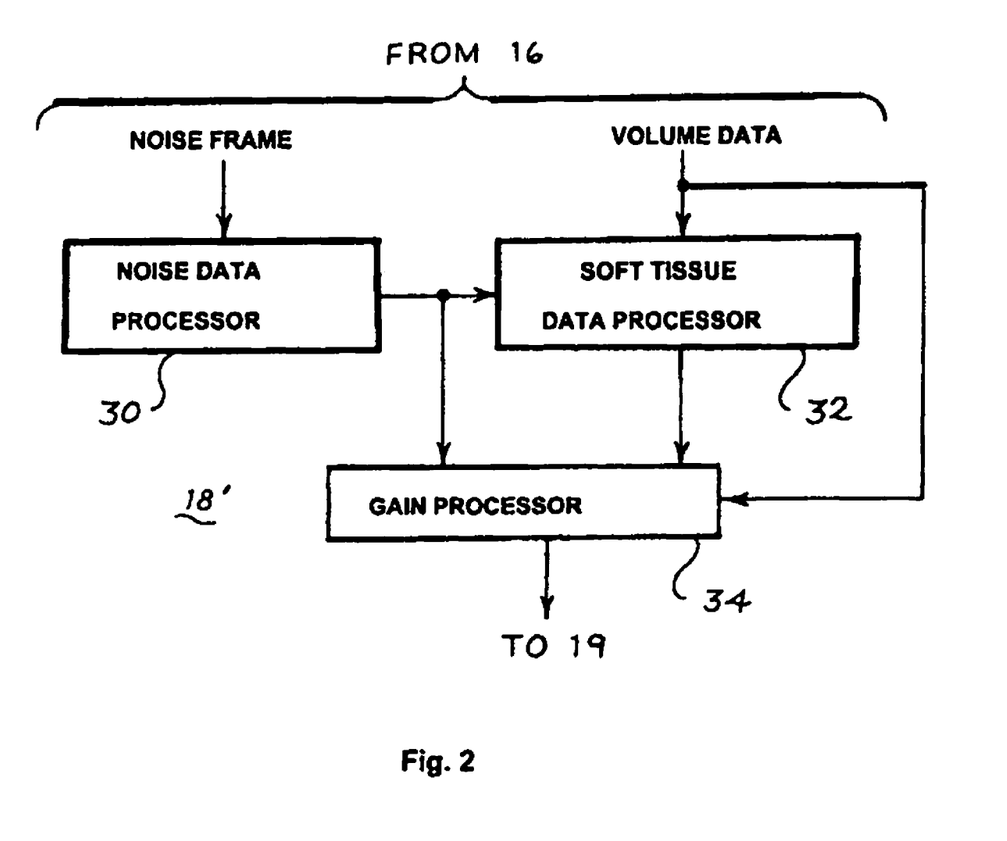
FIG. 2 is a block diagram of an embodiment of an adaptive multidimensional back-end mapping stage of FIG. 1.
Figure 3:
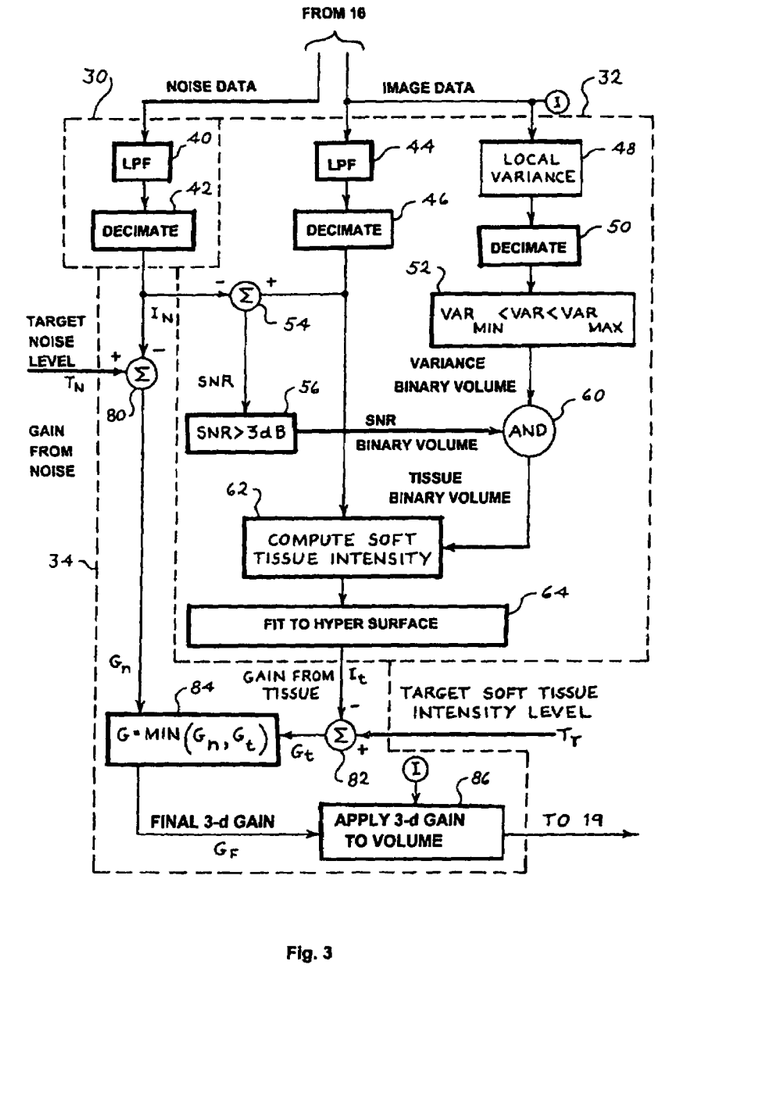
FIG. 3 is a more detailed block diagram of one embodiment of the mapping stage of FIG. 2.

FIGS. 2 and 3 show an embodiment to control the local gain throughout the volume such that soft tissue is displayed at a substantially constant target value. FIG. 2 provides a block diagram of these embodiments of a mapping stage 18' of FIG. 1. As shown in FIG. 2, the mapping stage 18' includes a noise data processor 30, a soft tissue processor 32, and a gain processor 34. The noise data processor 30 generates an estimate of electronic noise as the noise varies through the volume. The soft tissue processor 32 generates a smoothed hypersurface indicative of the intensity of soft tissue within a volume at various locations in the volume. The gain processor 34 uses outputs from the processors 30 and 32 to adaptively adjust either the gain or both the gain and the dynamic range applied to the volume. In alternative embodiments, the noise data processor 30 is not provided.

Figure 4:
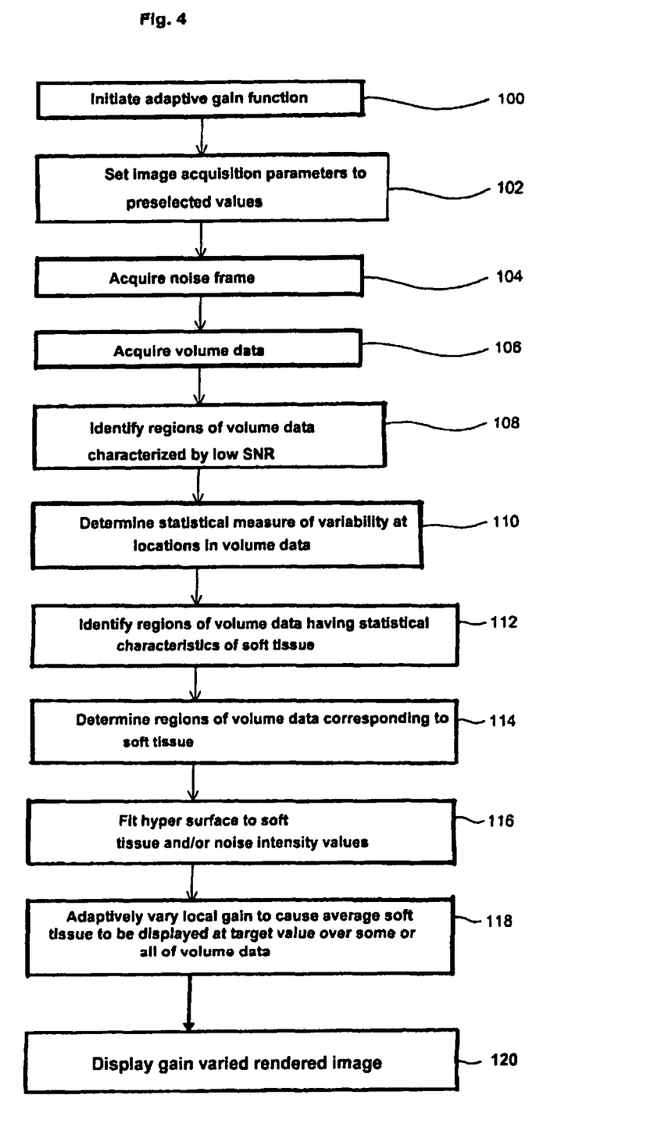
FIG. 4 is a flowchart of a method implemented by the embodiment of FIG. 3.

FIG. 3 provides a more detailed block diagram of the one embodiment of the elements of FIG. 2. FIG. 4 provides a flow chart of a method implemented by the embodiment of FIG. 3.

As shown in FIG. 3, the noise data processor 30 in this embodiment includes a low pass filter 40 and a decimator 42, and the processor 30 generates a measure of electronic noise at various locations distributed throughout the volume. The noise processor 30 accepts as an input a noise volume, i.e. data representing a volume acquired with the transmitters turned off. In the absence of an insonifying pressure wave, the resulting input signal forms a noise dataset that is a measure of currently prevailing system noise as a function of position within the volume. The low pass filter 40 smoothes the noise volume, and the decimator 42 decimates the filtered noise to a coarser grid, measuring for example 50 pixels on each dimension. Other decimation factors can be used, such as a decimation factor of 10×10×10 pixels on the acoustic or volume grid or no decimation. The noise volume provides the local noise of the system as a function of position within the volume.

The soft tissue processor 32 responds to an image volume of data which is acquired with imaging parameters and which includes data from soft tissue in the image. The soft tissue processor 32 identifies data in the volume dataset corresponding to soft tissue. For example, the soft tissue processor 32 includes a low pass filter 44 and a decimator 46 that are the same or different than the corresponding elements of the noise processor 30. The filtered, decimated noise volume from the noise processor 30 is summed with negative polarity with the filtered, decimated image volume in a summer 54. Since the noise volume and the image volume are in this example post-detection, post-log-compression signals, the summation performed by the summer 54 generates an output signal equal to the signal-to-noise ratio (SNR) for the associated regions of the two volumes. This SNR data is applied to a comparator 56 that generates as an output an SNR binary volume. This binary volume is set equal to one in regions of the volume characterized by an SNR greater than a predetermined value, e.g., 3 dB or 6 dB, and to zero in regions where the SNR is less than or equal to the predetermined value. Thus, the SNR binary volume identifies regions of the image volume that have a sufficiently high SNR to be candidates for soft tissue image data. The portions of the SNR binary volume characterized by the logic value zero correspond to high-noise, low-SNR regions of the image, and these regions are not considered candidates for soft tissue.

The soft tissue processor 32 also generates a variance binary volume with a local variance calculator 48, a decimator 50 and a comparator 52. These elements use the local spatial variance of the volume dataset to identify regions of the volume dataset having a variance characteristic of soft tissue.

In soft tissue, there are a large number of scatterers present in each resolution cell. Fully developed speckle occurs due to random interference between the reflected signals, and the amplitude of the signal obeys the Rayleigh distribution in regions of the volume dataset depicting soft tissue. In this embodiment, the degree to which local variance, calculated in a neighborhood of resolution cells around each voxel, resembles that of fully developed speckle is used as a measure of the likelihood that a particular voxel represents soft tissue. The variance binary volume is set equal to one in regions where the variance is consistent with soft tissue imaging and to zero otherwise.

The local variance calculator 48 operates by dividing the volume dataset into a grid of sub-volume regions. The size of these regions may be on the order of 10 times longer along each axis than the resolution size of the volume dataset. Smaller or larger sizes may be used.

The decimator 50 operates at the same or different scale as the decimators 42 and 46. The decimated variance volume is then compared voxel by voxel with minimum and maximum variance levels in the comparator 52. This comparison is particularly straightforward for log compressed data, where the variance of fully developed speckle characteristic of soft tissue is 2*(5.57 dB). Thus, regions of soft tissue in the volume are characterized by fully developed speckle having a variance close to 2*(5.57 dB). Any threshold may be used. The actual local variance of speckle may not be equal to the theoretical value due to filters in the signal processing path of the ultrasound system. In practice, the variance is determined through measurements on phantoms mimicking soft tissue.

Electronic noise has a variance close to that of soft tissue, and the AND operation indicated at 60 uses the SNR binary volume and the variance binary volume to avoid misclassification of electronic noise as soft tissue. This AND operation is performed on a voxel-by-voxel basis of the decimated SNR binary volume and the decimated variance binary volume. The resulting decimated tissue binary volume has a value equal to zero if either the SNR binary volume indicates that the associated region is characterized by low SNR ratio or the variance binary volume indicates that the associated region is not soft tissue. The SNR binary volume is not required in all embodiments, and other techniques can be used to avoid misclassifying regions of the image dominated by noise as soft tissue. For example, noise reduction techniques can be applied prior to local variance estimation.

The filtered, decimated image volume dataset from the decimator 46 and the binary tissue volume dataset from the AND element 60 are applied as inputs to a processor 62 for computing soft tissue intensity. In particular, the output of the processor 62 is a decimated dataset having intensity values that depend upon the corresponding values of the tissue binary volume in the same region. Where the corresponding region of the tissue binary volume is equal to logic value zero (indicating that the region does not correspond to soft tissue), the output of the processor 62 does not include an intensity value for the corresponding region. Alternatively, for regions where the tissue binary volume is equal to logic value one, the output of the processor 62 includes the intensity value for the corresponding region as filtered by the filter 44 and decimated by the decimator 46.

In another embodiment, the processor 32 identifies data corresponding to soft tissue as a function of moments calculated from the volume dataset. For example, the processor 32 filters voxels of B-mode intensities. Any size kernel may be used, such as 3×3×3. Symmetrical or asymmetrical kernels may be used. For each voxel without decimation or each remaining voxel after decimation, the surrounding neighborhood of voxels within the volume contribute to the filtered output. The filtering applies the first, second or higher moment. For a first moment, the voxels in the kernel are averaged. For a second moment, the voxels in the kernel are each squared, summed, and then normalized. Both the first and the second moments may be used. A threshold indicates whether the resulting moment indicates soft tissue, such as a second moment above a threshold indicating soft tissue. For using multiple moments or soft tissue measurements, a combination of thresholds or a combination of measurements with a single threshold may be used to identify soft tissue. For example, regions with first and second moments exceeding first and second thresholds, respectively, correspond to soft tissue and other regions do not.

In one embodiment, the processor 32 identifies different types of soft tissue. Different types of soft tissue may have different response characteristics. For example, ranges of first, second and/or higher moments may indicate the type of tissue. Appropriate functions or thresholds identify intensities or voxels associated with different types of tissue. Other embodiments for identifying one or more types of soft tissue may be used.

In processor 64, a hypersurface is fitted to the volume dataset supplied by the processor 62. A decimated or non-decimated dataset is used for fitting. The data within the volume for fitting is soft tissue data. Non-soft tissue data is not used. Any function defining the hypersurface may be used, such as a polynomial function. In one embodiment, a linear or quadratic function defines the hypersurface. The hypersurface is fit in three spatial dimensions (i.e., the volume) with a fourth dimension being the input data for soft tissue, such as intensities associated with soft tissue.

The hypersurface provides a measure of local average soft tissue intensity as the hypersurface varies throughout the volume. The average is a fitted to local data. The variation is spatially low in order to preserve imaging details, such as by limiting the hypersurface by the polynomial of a low order or other function. In one embodiment, the soft tissue data is fit without noise consideration. In another embodiment, the SNR binary volume is used to avoid corruption of the hypersurface by portions of the volume dominated by noise. Where the hypersurface is fitted to a decimated volume of soft tissue data, the hypersurface fitted by processor 64 does not vary so rapidly as to interfere with the presentation of transitions or interfaces between soft tissues of different contrasts. In one embodiment, the processor 64 divides the volume into a 6×6×6 or other grid, calculates the average soft tissue intensity value for each region of the grid, and then fits the hypersurface to the average values.

The processor 64 may determine separate hypersurfaces for different types of data. For example, one dataset is of soft tissue data of one type, and another dataset is of soft tissue data of another type. The two datasets include data identified from the input dataset representing the volume. Different hypersurfaces are fitted, one for each type of soft tissue data. As another example, an additional hypersurface is determined for noise. The hypersurface is fit to a noise volume dataset.

The gain processor 34 is operable to map the data of the input volume to output values as a function of the hypersurface. The data to be mapped includes the soft tissue data and may include other data. For example, the input volume dataset is mapped rather than the dataset derived there from to indicate soft tissue.

The gain processor 34 of this embodiment uses a summer 82 to obtain the difference between the fitted hypersurface from the processor 64 and a soft tissue target intensity level $T_T$ on a region-by-region or voxel-by-voxel basis. The output of the summer 82 is a tissue gain $G_T$, which varies with range, elevation, and azimuth and is the gain required to cause the hypersurface fitted to the local tissue mean to be displayed at the soft tissue target level $T_T$.

In one embodiment, only the gain for mapping to the target tissue level is applied. In another embodiment, this tissue gain $G_T$ is applied to a logic block 84 that also receives a second input $G_N$. The signal $G_N$ is generated by a summer 80 that takes the difference on a voxel-by-voxel or region-by-region basis between a noise target level $T_N$ and corresponding values of the filtered, decimated noise volume dataset or a noise hypersurface. Thus, the noise gain $G_N$ also varies with range, elevation, and azimuth, and represents the gain to ensure that the local mean noise level is presented at the noise target level $T_N$. The logic block 84 sets the final three-dimensional gain equal $G_F$ to the lesser of $G_N$ and $G_T$. This final three-dimensional gain $G_F$ is applied to the image volume dataset in block 86. The gain processor 34 sets the gain $G_F$ in such a way that the soft tissue regions of the volume are displayed at about the tissue target level $T_T$ for all portions of the volume where the noise signal is less than the noise target level. In regions of the volume where the noise intensity $I_N$ is greater than a noise target level $T_N$ a lower gain is used to ensure that noise is not amplified inappropriately.

In some embodiments, the final gain $G_F$ is decomposed into depth gain, azimuth lateral gain, elevation lateral gain, azimuth lateral gain slope, and elevation lateral gain slope components, e.g. via a least squares fit. It may be preferable to chose depth gain components to minimize azimuth and/or elevation lateral gain slope values, and the master gain value to minimize changes in depth gain, azimuth lateral gain, and elevation lateral gain.

In one embodiment, the target tissue intensity level is constant throughout the volume, but may vary in other embodiments. The hypersurface provides a difference from the target level throughout the entire volume, even for locations not associated with soft tissue. Due to the fitting of the hypersurface and restriction to slow variation, the resulting gain may not be largely different for tissue and non-tissue regions. When data representing non-tissue regions is gain adjusted, the intensity levels will remain different than for soft tissue regions.

In other embodiments, multiple hypersurfaces are used for mapping. A combination of setting the gain and dynamic range may be used. For example, setting the gain and the dynamic range may allow mapping of different types of tissues to or near different target tissue levels. Alternatively, the different hypersurfaces are applied to different subsets of the volume dataset, are combined to form one hypersurface using any priority or function, or are used for separate renderings. For example, a noise hypersurface provides a negative gain adjustment. The difference between the target tissue value and the soft tissue hypersurface is increased to account for contribution of noise.

FIG. 4 provides a flowchart of a method implemented by the system of FIG. 3, but a different system may be used. A medical ultrasonic imaging system implements the method for adaptively controlling gain. Additional, different, or fewer acts may be provided. For example, the noise-based acts 104, 108, and 114 are not performed. As another example, different identification of soft tissue regions than represented by acts 110, 112, and 114 may be used. The acts are performed in the order shown or a different order.

In act 100, the adaptive gain features described are initiated. This can be done in many ways. For example, adaptive gain can be initiated in response to user request or automatically at intervals. For example, adaptive gain can be automatically initiated every set number of volume scans or seconds. As another example, a detected change may trigger calculation of the gain.

Once adaptive gain has been initiated in block 100, the three-dimensional imaging acquisition parameters of the system are set to preselected values in act 102. These preselected values optimize operation of the adaptive gain processor. By way of example, the following general guidelines have been found suitable in one embodiment: gain and dynamic range are determined so that, for the widest possible variety of imaging situations, the highest possible signal-to-noise ratio is maintained over the entire volume without causing saturation of any portion of the volume. This ensures that regions where the signal is weak are taken into account by the adaptive gain processor. Other parameters and/or goals may be used. The preselected values may be changed or altered by the user. The preselected values may be adaptive to received data. The preselected values may be different for different imaging applications.

Once the image acquisition parameters have been selected, they are used to acquire one or more noise datasets in act 104 and an image volume dataset in act 106. For example, the noise volume dataset is a conventional image dataset, except that the transmitters are turned off. The receivers and processor receive signals by scanning through the volume. Since the transmitters are turned off, there is no bona fide echo signal, and any signal appearing in the dataset is representative of system or electronic noise. The noise volume dataset is used in block 108 to identify regions characterized by low SNR. The image volume dataset can be in any desired modality, and can, for example, include fundamental or harmonic imaging of tissue with or without added contrast agent.

Acts 110, 112, and 114 operate to identify voxels of the input volume data corresponding to soft tissue. For example, a dataset of B-mode intensities representing a volume is acquired in act 106 and processed to determine voxels or regions associated with soft tissue.

In act 110, a statistical measure of variability is determined for the input volume data, such as each voxel or selected regions. In act 110, the spatial or temporal mean of amplitude-detected, log-compressed signals can be used as a first moment. Alternately, the spatial variance of noise power normalized by the local mean of noise power can be used as the second moment. For example, a normalized spatial variance can be determined on a pre-compression signal, where the normalized spatial variance is normalized by the local mean of the pre-compression signal. The first, second or higher moment of a probability distribution with a three-dimensional kernel. The four dimensional space corresponds to three spatial dimensions and a data (e.g., intensity) dimension.

Each statistical measure is a function of a three-dimensional region around each voxel or region of the input volume data. The region may be of any size, such as being an N×M×P region, each of N, M, and P being greater than 2. Larger regions may be used. The region is symmetrical or asymmetrical. The region corresponds to voxel spacing without decimation or after decimation.

The statistical measure of variability may be calculated along any one of the lateral, axial, and elevation axes, any two of these axes, or all three axes. The example described above calculates the variance over three spatial dimensions, such as the elevation, azimuth, and axial axes. The three spatial dimensions may be in a volume domain (e.g., x, y, z) or the scan domain (range, elevation, azimuth).

In acts 112 and 114, regions of the image volume dataset corresponding to soft tissue are determined. Voxels of the input volume data corresponding to soft tissue are determined based at least in part on one or more of the statistical measures. Thresholds or other functions may be used to indicate soft tissue information from other information. Any technique may be used, such as the soft tissue detection or techniques to assist in soft tissue detection disclosed in U.S. Pat. No. 6,579,238. In one embodiment, both the first and second moments are used. More than one type of soft tissue may be identified, such as by applying different thresholds.

In act 114, the regions of the volume characterized by low SNR as determined in block 108 are used to ensure that regions identified as soft tissue are outside of the noise-dominated regions of the image. The local coherence factor may be used to ensure that regions of high acoustic noise or clutter are excluded from mapping decisions. The local coherence factor is defined as the ratio of the coherent (phase-sensitive) to the incoherent (phase-insensitive) summation across the receive channels of the delayed and apodized signals. See the discussion of Rigby U.S. Pat. No. 5,910,115. A low coherence factor indicates strong phase aberration, i.e., high levels of acoustic noise or clutter. Using the coherence factor, the regions of the volume dominated by clutter can be ignored.

As explained above, this soft tissue identification can be done based on statistical measures of variability. Alternately, other methods may be used for identifying soft tissue, as for example methods based on the magnitude of the image signal. See the discussion of Klesenski U.S. Pat. No. 5,579,768.

Using the soft tissue information within the volume, spatial variations in intensity or other data are extracted. The extraction is provided by a three-dimensional hypersurface embedded in four-dimensional space. The four dimensions of the space are three spatial dimensions and a fourth intensity or data dimension.

At act 116, a three-dimensional hypersurface is fit to the soft tissue voxels (e.g., B-mode intensity values) over an entire volume with or without decimation. The hypersurface is fit along three spatial dimensions. Any now known or later developed algorithm or process for fitting a hypersurface may be used. In one embodiment, the hypersurface is based on a polynomial function. A best fit of a three-dimensional surface satisfying the limitations of the polynomial to the soft tissue data is determined. A linear, second order, or other polynomial function may be used. A hypersurface is generally described by an equation of the form $F(x, y, z, w \ldots) = 0$. Where the variables $x, y, z, w \ldots$ correspond to the dimensions of the n-dimensional space where the hypersurface is embedded. In the special case where F is a polynomial of the second degree the hypersurface is called a second order hypersurface. Different hypersurfaces may be used for different applications, such as providing for a more slowly varying hypersurface for imaging more uniformly responsive organs. Any technique may be used, such as the fitting techniques disclosed in U.S. Pat. No. 6,579,238.

More than one hypersurface may be fit. For example, hypersurfaces are fit to different datasets. The datasets represent response from different tissues or tissue and noise. The same type of hypersurface is independently fit to the different datasets. Alternatively, different hypersurfaces are fit to the different datasets, such as providing different constants or polynomials for fitting the different hypersurfaces.

At act 118, the local gain is varied adaptively to cause signals having the amplitude of the hypersurface at the respective locations to be displayed at or near a soft tissue target value over some or the entire image. The gain is used to map the input volume dataset and/or different volume datasets (e.g., subsequently acquired datasets representing the volume). The hypersurface provides data adaptive variation in the gain as a function of location within the volume. The voxels are mapped to a soft tissue range of output values. An average amplitude of regions of soft tissue in the image to be rendered is substantially at the target display value. Substantially accounts for mapping to a range of values, such as within 10 intensity levels.

The soft tissue target value or target display value can be set in many ways. The target display value may simply be a stored value or may be a user-selected value, or it may be a value adaptively determined in response to ambient light. Alternatively, the soft tissue target level is a function of the currently invoked post-processing curve. Specifically, a user controllable or predefined value may be used as a target soft-tissue gray level $T_G$. $T_T$ is then defined whenever a post-processing curve is selected to be the signal intensity level that is mapped to the display gray level of $T_G$. Other factors may be considered in setting the gain, such as noise, SNR, or dynamic range.

To map for more than one hypersurface, both a gain and another setting may be used. For example, the dynamic range varies as a function of two or more three-dimensional hypersurfaces. The gain may also be a function of the two or more hypersurfaces. Alternatively, the gain is a function of one hypersurface, and the other setting is a function of another hypersurface.

Multiple hypersurfaces may be used, such as for two or more different types of tissue or tissue and noise. For example, noise signals are provided in three-dimensions and are indicative of a currently prevailing noise, such as clutter, electronics noise, aberration or other noise. A noise hypersurface is fit to the noise signals. The gain or other setting adaptively varies as a function of the noise hypersurface. The gain may also be a function of the hypersurface for tissue. For example, the hypersurfaces or resulting gain values are combined by either choosing the minimum gain at a particular voxel location or averaging them.

In act 120, an image is displayed as a function of the data output from the mapping. The data may be filtered, interpolated to a three-dimensional grid, or otherwise processed before rendering. The output data includes voxels representing a volume or distributed for multiple voxels along each dimension. Ray casting, intensity projection (minimum, maximum, average), surface rendering, or other volume rendering is performed using the output data. Alpha blending, opacity, shading, or other rendering processes may be used. A transform function may be applied. Rendering creates a three-dimensional representation from a viewing direction on the two-dimensional screen.

Many alternatives are possible. In fact, the widest range of analog and digital signal processing techniques can be used to implement the basic functions described above. A programmed computer is one implementation for the adaptive gain processor described above. For example, the adaptive gain and optionally the adaptively determined dynamic range can be applied to the image signals at any desired point along the signal path between the transducer array 13 and the display 19. Both can be applied before or after scan conversion, log compression and detection. The adaptive gain processor can operate on RF, IF or baseband signals before or after detection, log compression, and scan conversion.

In the foregoing examples, the input signal is adaptively mapped to a soft tissue or a noise range of output signal values by appropriately controlling various back-end gain stages. However, front-end gain stages may be varied in gain to obtain the desired output signal values, either alone, or in combination with gain variations in one or more back-end gain stages.

The foregoing detailed description has been intended by way of illustration and not limitation. It is only the following claims, including all equivalents, that are intended to define the scope of this invention.

The invention claimed is:

1. A system for equalizing tissue information in medical diagnostic ultrasound imaging, the system comprising:
a processor operable to determine a hypersurface as a function of ultrasound data representing a volume and operable to map the data to output values as a function of the hypersurface; and
a display operable to display an image responsive to the output values;
wherein the processor is configured to identify different types of soft tissue in the data representing the volume, the different types of soft tissue being identified as different from each other, the processor configured to determine the hypersurface for one of the different types of soft tissue and to determine an additional hypersurface for another one of the different types of soft tissue, and the processor configured to map the data to the output values as a function of both the hypersurface and the additional hypersurface, the processor configured to map by selecting between the hypersurface and the additional hypersurface for each voxel, by using the hypersurface for a first type of setting and use the additional hypersurface for a second type of setting, by mapping with two different target tissue levels, by combining the hypersurface and the additional hypersurface, or by using the hypersurface for a first rendering and using the additional hypersurface for a second rendering.

2. The system of claim 1 wherein the processor is configured to determine the hypersurface by fitting the hypersurface in three spatial dimensions to the data, the data comprising ultrasound intensities, the fitting being a function of a polynomial.

3. The system of claim 1 wherein the processor is configured to identify data corresponding to soft tissue as a function of moments calculated for different neighborhoods of data within the volume, the processor configured to determine the hypersurface as a function of the data corresponding to soft tissue and not other data of the volume.

4. The system of claim 1 wherein the processor is configured to determine a noise hypersurface for noise, and the processor configured to map as a function of the hypersurface and the noise hypersurface.

5. The system of claim 1 wherein the processor is configured to map voxels to a soft tissue range of output values.

6. The system of claim 1 wherein the hypersurface is described by a polynomial.

7. The system of claim 1 wherein the hypersurface is a second order surface.

8. The system of claim 1 wherein the processor is configured to cause an average amplitude of regions of soft tissue in the image to be displayed at substantially a target display value.

9. The system of claim 1 wherein the processor is configured to identify voxels of the data corresponding to soft tissue by:
determine statistical measures of variability of the data, each statistical measure being a function of a three-dimensional region around each voxel of the data; and
identify the voxels of the data corresponding to soft tissue based at least in part on the statistical measures.

10. The system of claim 9 wherein the statistical measures comprise a second moment of a N×M×P region, each of N, M, and P being greater than 2.

11. The system of claim 1 wherein the processor is configured to provide noise signals in three-dimensions indicative of a currently-prevailing noise and fit a noise hypersurface to the noise signals, wherein the map is for adaptively varying gain as a function of the hypersurface and the noise hypersurface.

12. The system of claim 1 wherein the data comprises B-mode intensities, and wherein the hypersurface comprises three spatial dimensions fit to the B-mode intensities.

13. The system of claim 1 wherein a first set of voxels of the data corresponds to the first type of the soft tissue, and a second set of voxels of the data corresponds to a second type of the soft tissue, wherein the processor is configured to fit the hypersurface to the voxels of the first set and the additional three-dimensional hypersurface to the voxels of the second set, and wherein the processor is configured to map by varying dynamic range as a function of the hypersurface and the additional hypersurface.

14. The system of claim 1 wherein the processor is configured to map the different types of the tissues to the different target tissue levels as a function of the hypersurface and the additional hypersurface.

15. The system of claim 1 wherein the processor is configured to map by applying the hypersurface to the data for the one type of the tissue and applying the additional hypersurface to the data for the other type of the tissue.

16. The system of claim 1 wherein the processor is configured to combine the hypersurface with the additional hypersurface.

* * * * *